United States Patent [19]

Pigiet et al.

[11] Patent Number: 4,904,602

[45] Date of Patent: Feb. 27, 1990

[54] THIOREDOXIN SHUFFLEASE AND USE THEREOF

[75] Inventors: Vincent P. Pigiet, Winchester; James R. Rusche, Worcester, both of Mass.; Barbara J. Schuster, State College, Pa.

[73] Assignee: Repligen Corporation, Cambridge, Mass.

[21] Appl. No.: 894,421

[22] Filed: Aug. 8, 1986

Related U.S. Application Data

[63] Continuation-in-part of Ser. No. 802,569, Nov. 27, 1985, abandoned.

[51] Int. Cl.[4] .......................... C12N 9/06; C12N 9/02
[52] U.S. Cl. .................................. 435/191; 435/189; 935/29
[58] Field of Search ................ 435/189, 191; 530/331, 530/350; 935/29

[56] References Cited

U.S. PATENT DOCUMENTS 4,421,685 12/1983 Chance et al. .................. 260/112.7

OTHER PUBLICATIONS

Morgenstern, R., et al, (1983) Chemical Abstracts 99:135967k.
Enzyme Nomenclature (1978) Academic Press, New York, pp. 186–189.
Holmgren, A. (1981) TIBS, 26–29.
Wallace, B. J. and Kushner, S. R. (1984) "Genetic and physical analysis of the thioredoxin (trxA) gene of *Escherichia coli* K-12" 32:399–408.

*Primary Examiner*—Thomas G. Wiseman
*Assistant Examiner*—Charles L. Patterson, Jr.
*Attorney, Agent, or Firm*—Roman Saliwanchik; David R. Saliwanchik

[57] ABSTRACT

The subject invention concerns a novel enzyme named thioredoxin shufflease, means for preparing the same, and procedures for using thioredoxin shufflease to fold proteins containing disulfide crosslinks. Thioredoxin shufflease is a generic term to define enzymes which have the following characteristics: (a) contain a single reactive thiol group; (b) catalyze the exchange of disulfides in a protein undergoing the refolding process; and (c) are not consumed in the oxidation/refolding process. Specifically exemplified is a thioredoxin shufflease produced from an *E. coli* thioredoxin gene.

10 Claims, No Drawings

THIOREDOXIN SHUFFLEASE AND USE THEREOF

CROSS REFERENCE TO A RELATED APPLICATION

This is a continuation-in-part of our copending application Ser. No. 802,569, filed on Nov. 27, 1985, now abandoned.

BACKGROUND OF THE INVENTION

When proteins that contain disulfide bonds are produced in microorganisms they are made in a reduced form that lacks the critical and correct disulfide bonds required for activity. On cell breakage, these proteins are often insoluble because of their non-native conformations and have non-native incorrect disulfide pairing. Various approaches have been used to correctly fold these proteins, which generally require reduction of all disulfides followed by carrying out a controlled oxidation reaction. This controlled oxidation reaction must provide a suitable oxidation environment to oxidatively transform protein thiols into disulfides as well as to allow for the necessary exchange reactions. Conditions that promote effective disulfide interchange require a balance between oxidation and reduction such that the greater thermodynamic stability of the native, or correct, disulfides will be the driving force for achieving the native structure. A consequence of this necessary balance between the need for oxidative drive for disulfide formation and a suitable redox environment for disulfide exchange is that either too high or too low an oxidation environment will compromise the yield of native protein. Examples of incorrectly folded proteins include undesirable disulfide isomers (i.e., with incorrect disulfide pairs) or molecules with intermolecular disulfide pairs forming oligomers of the desired protein products.

Perhaps the most commercially important protein containing disulfide bonds is insulin. U.S. Pat. No. 4,421,685 discloses a process for producing insulin wherein the S-sulfonated form of the A-chain and the S-sulfonated form of the B-chain are reacted with a thiol reducing agent under specific conditions to form insulin. Thiol reducing agents disclosed therein are dithiothreitol (DTT) and dithioerythritol (DTE).

BRIEF SUMMARY OF THE INVENTION

The present invention utilizes a protein enzyme that mimics the natural biological process for protein folding. The enzyme, here termed thioredoxin shufflease, is characterized as having a single reactive thiol that serves to catalyze the exchange of disulfides in a protein undergoing the refolding process. Unlike the various oxidizing agents commonly used, including thiols such as glutathione and dithiothreitol, organic oxidants such as idosobenzene, or oxygen, all of which are consumed in the oxidation/refolding process, thioredoxin shufflease, advantageously, is recycled, as expected for a true catalyst. Also, because thioredoxin shufflease acts as a non-consumed catalyst the molar amounts utilized are small, amounting to only a fraction of the amount of protein being refolded. This latter point is important not only for economic considerations, but also for considerations of removal of the thioredoxin shufflease from the final refolded product.

The subject invention also concerns the genetic construction of a hybrid gene coding for thioredoxin shufflease, and a process for producing thioredoxin shufflease. Further, the invention concerns the use of thioredoxin shufflease for the catalytic refolding of reduced, unfolded proteins and scrambled proteins where incorrect disulfide bonds have been formed (i.e., the protein is folded but in the wrong conformation, with only a fraction being active). Still further, the invention concerns the use of thioredoxin shufflease for the catalytic refolding of a recombinant protein in a crude cell extract.

Examples of proteins containing disulfide crosslinks which can be refolded by thioredoxin shufflease are insulin, proinsulin, bovine pancreatic ribonuclease (RNase), lysozyme, bovine pancreatic trypsin inhibitor, interferon, rennin, plasminogen activator, prolactin, human α-1 trypsin inhibitor, Factor VIII, and the like.

The above proteins, and others containing disulfide crosslinks, can be used in their S-sulfonated form as starting material in the invention disclosed herein. When the S-sulfonated form of the protein is used, reduced thioredoxin shufflease is added to the folding process.

DETAILED DESCRIPTION OF THE INVENTION

Thioredoxin shufflease is a generic term to define enzymes which have the following characteristics: (a) contain a single reactive thiol group; (b) catalyze the exchange of disulfides in a protein undergoing the refolding process; and (c) are not consumed in the oxidation/refolding process.

Specifically exemplified herein is a thioredoxin shufflease producible when an *E. coli* thioredoxin gene is mutated at codon 35 to change cysteine (TGC) to a codon coding for any of the other 19 amino acids, i.e., alanine, arginine, asparagine, aspartic acid, glutamine, glutamic acid, glycine, histidine, isoleucine, leucine, lysine, methionine, phenylalanine, proline, serine, threonine, tryptophan, tyrosine, and valine. This alteration changes the dithiol thioredoxin compound to a monothiol compound which is referred to as thioredoxin shufflease.

Site-directed mutagenesis was used to change *E. coli* thioredoxin gene to an *E. coli* thioredoxin shufflease gene. This process required changing the codon corresponding to Cys35 (TGC) to a sequence encoding another amino acid (in the example given here, Cys35 was changed to Ser35). To accomplish this mutagenesis procedure the cloned thioredoxin gene (genetic designation TRX) was recloned to the well-known single strand DNA phage MP19.

Other thioredoxin, thioredoxin-derived, or thioredoxin-like gene sources, as described infra, can be used in place of the *E. coli* source.

The cloning of the hybrid gene coding for thioredoxin shufflease was initiated by isolating plasmid pBHK8 from the well-known strain of *E. coli* designated *E. coli* strain 3981 (Lunn, C. A., Kathju, S., Wallace, B. J., Kushner, S. R. and Pigiet, V. [1984] J. Biol. Chem. 259:10469–10474) by standard procedures. pBHK8 DNA was cleaved with KpnI and PvuII and MP19 replicative form DNA was cleaved with restriction endonucleases KpnI and HincII. The DNA samples were mixed and ligated with T4 DNA ligase. DNA was transformed to competent *E. coli* JM103 and the cells spread on nutrient agar plates. Recombinant phage unable to utilize lactose (white plaques) were amplified and single strand phage DNA was prepared and examined by agarose gel electrophoresis. Those recombinants containing the thioredoxin gene were identified by the size of DNA inserted (2.8 kilobases) and DNA sequencing. The recombinant phage containing the thioredoxin gene is referred to as TRX 4. The nucleotide sequence of the thioredoxin gene is disclosed in Wallace, B. J. and Kushner, S. R. (1984) Gene 32:399–408. This sequence is incorporated herein by reference to this publication.

A thioredoxin shufflease gene was constructed from the *E. coli* thioredoxin gene by oligonucleotide-directed mutagenesis (Zoller, M. J. and Smith, M. [1983] Methods in Enzymol. 100:468–500).

A 27 base oligonucleotide 5'-TGG TGC GGT CCG AGC AAA ATG ATC GCC, corresponding to the complimentary sequence in the region of cysteine residue 35 (i.e., codon AGC underlined), was annealed to single strand TRX DNA and extended with Klenow DNA polymerase in vitro. The polymerization mixture also contained *E. coli* single strand binding protein and T4 DNA ligase. The DNA was transformed into competent JM103 cells.

Those recombinant clones containing the base change at codon 35 (i.e , TGC to AGC) were identified by differential DNA hybridization with a radioactive oligonucleotide spanning codon 35 (5'-C GGT CCG AGC AAA AT), corresponding to the sequencing for the modified protein. A higher melting temperature of the duplex DNA was observed with 2 of the 20 clones. One of these two thioredoxin derivative clones (TRX 351) was replaque isolated to insure a homogenous clone and single strand DNA was prepared. Dideoxy sequencing of the thioredoxin-derived gene confirmed a single base change at codon 35 from TGC to AGC.

The TRX 351 gene product (termed thioredoxin shufflease) can be prepared from cell cultures infected with the M13 phage containing the thioredoxin shufflease gene (TRX 351) using standard procedures.

The thioredoxin shufflease gene can be transferred to a plasmid vector by standard procedures. Duplex DNA prepared by extension on TRX 351 DNA of the M13 sequencing primer (New England Biolabs, Beverly, Mass.) with Klenow polymerase allows excision of restriction fragments containing the TRX 351 gene (KpnI/PstI). For example, pUC18 digested with KpnI and PstI was mixed with the KpnI/PstI fragment of TRX 351 and ligated with T4 DNA ligase. Recombinant clones were obtained by transformation of competent cells with the DNA mixture and selection for ampicillin resistant colonies. Restriction digestion confirmed the insertion of a 2.8 kilobase DNA fragment.

Thioredoxins are low molecular weight dithiol proteins that have the ability to reduce disulfides in typical organic compounds such as Elman's reagent or disulfides as they exist naturally in a variety of proteins (Holmgren, A. [1981] Trends in Biochemical Science, 6, 26–39).

Thioredoxin and thioredoxin-derived, or thioredoxin-like, dithiol peptides which can be used as a source of the thioredoxin gene and thioredoxin shufflease are exemplified by the following compounds.

(1) thioredoxin isolated from *Escherichia coli* (Laurent, T. C., Moore, E. C., and Reichard, P. [1964] J. Biol. Chem., 239, 3436–3445):

(2) thioredoxins isolated from other sources, e.g., thioredoxin isolated from yeast (Porque, G. P., Baldesten, A., and Reichard, P. [1970] J Biol. Chem., 245, 2362–2379); *Cyanobacterium* (Gleason, F. K. and Holmgren, A. [1983] in "Thioredoxins, Structure and Function" [P. Gadal, ed.] Editions du Centre National de la Recherche Scientifique); rat (Guerara, J., Moore, E. C., and Ward, D. NM. [1983] ibid; T4 bacteriophage (Soderberg, B-O, Sjoberg, B-M, Sonnerstam, U., and Branden, C-I [1978] Proc. Natl. Acad. Sci. USA, 75, 5827–5830);

(3) thioredoxin-derived dithiol peptides representing peptides produced by cleavage of intact thioredoxins, as described infra. One such example of this class of thioredoxin-derived peptides is the fragment containing residues 1 through 37 (i.e., $T_{1-37}$) produced by cyanogen bromide cleavage of thioredoxin from *E. coli*. An important feature of these thioredoxin-derived dithiol peptides is that they contain the redox-active peptide sequence, Cys-X-Y-Cys-Lys, wherein X and Y, independently, can be any of the 20 amino acids. For example, the redox-active peptide sequence from *E. coli* thioredoxin is Cys-Gly-Pro-Cys-Lys (Cys=cysteine, Gly=glycine, Pro-proline, Lys=lysine); and (4) thioredoxin-like dithiol peptides that have the intrinsic ability to catalyze the reduction of protein disulfides. These thioredoxin-like dithiol peptides will generally have the characteristic of containing a pair of cysteine residues which form a redox-active disulfide. This example includes peptides, derived from natural sources or constructed synthetically, that include the same sequence as in *E. coli* thioredoxin, Cys-Gly-Pro-Cys-Lys, or analogous sequences from other thioredoxins such as that encoded for by T4 bacteriophage, Cys-Val-Tyr-Cys (Cys=cysteine, Val=valine, Tyr=tyrosine) (Soderberg, B-O, Sjorberg, B-M, Sonnerstam, U., and Branden, C-I [1978] Proc. Natl. Acad. Sci. USA, 75:5827–5830). Other thioredoxin-like peptides include the class of seed proteins called purothionins that have intrinsic thioredoxin-like activity (Wada, K. and Buchanan, B. B. [1983] in "Thioredoxins, Structure and function" [Gadal, P., ed], Editions du Centre National de la Recherche Scientifique).

Another source for the thioredoxin gene and thioredoxin shufflease is protein disulfide isomerase as disclosed in Edman, J. C., Ellis, L., Blacher, R. W., Roth, R. A. and Rutter, W. J. (1985) Nature 317:267–270.

Unfolded protein containing disulfide crosslinks can be efficiently folded by reacting the unfolded and reduced protein with an effective protein folding amount of oxidized thioredoxin shufflease, alone, or in combination with oxygen or a chemical oxidant such as dithiothreitol.

The concentration of thioredoxin shufflease which can be used in the invention process ranges from about 3 to about 50 $\mu$M. The optimal concentration appears to be at least 5 $\mu$M. It should be recognized that the precise level of thioredoxin shufflease can be readily ascertained for a particular protein by a person skilled in the protein art having possession of the subject invention.

Thioredoxin shufflease at a concentration of 5 $\mu$M catalyzes the refolding of reduced and denatured bovine pancreatic RNase (23 $\mu$M) to give quantitative recovery of enzymatic activity. The reaction can be carried on over a pH range of about 7.0 to about 11.0, as may be optimized for individual proteins. Preferrably, the pH range is about 7.0 to about 9.0. The rate of refolding was significantly greater than that of air and comparable to that of 20 mM oxidized DTT. With thioredoxin shufflease 50% activity was recovered after 51 hr compared to 50 hr using oxidized DTT. The rate of renaturation of RNase in the presence of air alone as the oxidant was too slow to be measured, with recovery of only 20% activity after 50 hr.

The time required for 50% reactivation of RNase ($T_{\frac{1}{2}}$) in the presence of thioredoxin shufflease can be decreased 4- to 8-fold (relative to refolding in the presence of air) with the addition of an oxidant such as oxygen and/or oxidized DTT. The $T_{\frac{1}{2}}$ for 5 μM of thioredoxin shufflease under $N_2$ was 80 hr. This value decreased to 50 hr with the addition of air and to 21 hr with the addition of oxygen. In the absence of thioredoxin shufflease, oxygen alone can catalyze a limited refolding of RNase with the recovered activity reaching a maximum of 30% after 30 hr. The same enhancement effect was observed with oxidized DTT. Under nitrogen, the $T_{\frac{1}{2}}$ for 5 μM thioredoxin shufflease decreased from 80 hr to 20 hr with the addition of 20 mM oxidized DTT. The $T_{\frac{1}{2}}$ in the presence of oxidized DTT alone (i.e., under nitrogen) was 56 hr. The best $T_{\frac{1}{2}}$ for 5 μM thioredoxin shufflease, 11 hr, was obtained using a combination of 20 mM oxidized DTT in the presence of oxygen.

Thioredoxin shufflease at a concentration of 5 μM with the addition of 20 mM DTT is as effective in refolding denatured, reduced RNase as 100 μM thioredoxin. In the presence of air the $T_{\frac{1}{2}}$ for thioredoxin shufflease with oxidized DTT was 18 hr compared to 20 hr for thioredoxin.

MATERIALS AND METHODS

Materials: Bovine pancreatic ribonuclease A (RNase) and cytidine-2':3'-cyclic monophosphate were obtained from Sigma, St. Louis, Mo. Thioredoxin was purified from *E. coli* SK3981 by the procedure of Lunn et al. ([1984] J. Biol. Chem. 259:10469–10474). 3-(N-morpholine)-propane sulfonic acid (MOPS) sodium was the ultrol grade from CalBiochem, San Diego, Calif. Sephadex G-25-50 was also obtained from Sigma. All other chemicals used were reagent grade.

Thioredoxin Shufflease Assay: Protein concentration was determined by the absorbance at 280 nm using a molar absorptivity of 13,700 $M^{-1} cm^{-1}$ (Holmgren, A. and Reichard, P. [1967] Eur. J. Biochem. 2:187–196). Protein concentration was also determined by quantitative rocket immunoassay as described by McEvoy et al. (McEvoy, M., Lantz, C., Lunn, C. A. and Pigiet, V. [1981] J. Biol. Chem. 256:6646–6650) using rabbit anti-thioredoxin. An anti-thioredoxin affinity column was prepared as described by Sjoberg and Holmgren (Sjoberg, B. M. and Holmgren, A. [1973] Biochim. Biophys, Acta. 315: 176–180) using the immunoglobulin fraction isolated by repeated ammonium sulfate precipitation. The antibody column retained approximately 1 mg of thioredoxin/ml of gel using a homogenous thioredoxin sample.

Affinity Purification of Thioredoxin 351: Dithiothreitol (0.04 mM) was added to 1 liter of medium obtained from a stationary phase cell culture of *E. coli* JM103 A179 infected with M13 TRX 351 and was incubated at room temperature for several hours. Immobilized antithioredoxin was added and the sample was agitated constantly at 4° C. overnight. The sample was then poured into a 3×10 cm column until all the anti-thioredoxin-sepharose was packed into the column. The medium was then passed over the column a second time. Finally, the column was exhaustively washed with 1M Tris, pH 7.4 until the absorbance at 280 nm was less than 0.03 to ensure removal of nonspecifically-bound protein.

Thioredoxin shufflease was eluted from the column with 0.1M acetic acid pH 2.2. The 0.7 ml fractions were immediately neutralized by the addition of 1M ammonium bicarbonate. The fractions were monitored for protein by absorbance at 280 nm. One large peak and a smaller shoulder peak were routinely observed. These fractions were pooled and concentrated under nitrogen using an Amicon stir cell with a YM10 filter (Amicon, Danvers, Mass.). The buffer was exchanged with 50 mM Tris, 3 mM EDTA, pH 7.4 by diluting and concentrating the sample. The sample was stored at 4° C.

Concentration and Activity of RNase A: Enzyme concentration of native and scrambled RNase were determined using an extinction coefficient of 9,800$M^{-1}cm^{-1}$ measured at 277.5 nm (Hantgan, R. R., Hammes, G. G. and Scheraga, H. A. [1974] Biochemistry 13:3421–3431). The concentration of the fully reduced enzyme was determined at 275 nm using an extinction coefficient of 9,200$M^{-1}cm^{-1}$ (Anfinsen, C. B., Haber, E., Sela, M. and White, F. H. Jr. [1961] Proc. Natl. Acad. Sci. USA 47:1309–1315).

The activity of RNase A was determined according to the procedure of Crook et al. (Crook, E. M., Mathias, A. P. and Rabin, B. R. [1960]Biochem J. 74:234–238). The final assay mixture consisted of 0.1M MOPS, pH 7.0, 7 mM cytidine-2':3'-cyclic monophosphate and 10–30 μg/ml RNase A. The increase of the absorbance at 291 nm upon the hydrolysis of cytidine-2':3'-cyclic monophosphate at 25° C. was monitored as a measure of RNase activity.

Renaturation and Refolding of Reduced and Denatured RNase A: Reduction and denaturation of RNase was performed by incubating overnight 30 mg of the native enzyme in 1.5 ml of 0.1M Tris/HCl, pH 8.6 containing 0.15M DTT and 6M guanidine.HCl. The reduced RNase was separated from excess DTT and guanadine.HCl by column chromatography using a 1×24 cm Sephadex G-25 superfine column equilibrated and developed with 0.01N HCl. Those fractions containing RNase A were pooled, the concentration determined by absorbance at 275 nm, and the fractions stored under argon frozen at −20° C.

Reoxidation of RNase A was initiated by diluting the reduced enzyme in 0.1M Tris, pH 7.4 or 9.0 with 1 mM EDTA containing various amounts of thioredoxin shufflease or thioredoxin. At various times aliquots were assayed and the percentage of refolding calculated by comparison of the specific activity (i.e., hydrolysis of cytidine-2':3'-cyclic monophosphate per milligram of RNase protein) with native, non-denatured RNase.

Renaturation and Refolding of Scrambled RNase: Scrambled RNase was produced by oxidation under denaturing conditions of the reduced and denatured RNase isolated as described in the previous section. The pooled fractions from the Sephadex G-25 column were made 6M in guanidine.HCl and the pH adjusted to pH 8.6 with solid Tris. Oxygen was then bubbled through for several minutes and the sample was incubated at room temperature protected from light for 3–4 days. The amount of free thiol determined by the method of Ellman (Ellman, G. L. [1959] Arch. Biochem. Biophys, 82: 70–77) was less than 0.05 mole per mole of RNase. The activity was about 5%, indicating that the majority of the refolded RNase was in an incorrect and inactive form.

Reactivation of scrambled RNase was initiated by diluting the inactive RNase into 0.1M Tris, pH 7.4 with 1 mM EDTA containing various amounts of thioredoxin shufflease and/or reduced DTT. At various times aliquots were assayed, and the percentage of reactivation was calculated by comparison of the specific activity with native RNase as previously described.

Thioredoxin Fragments $T_{1-37}$ and $T_{19-36}$:

(a) Production of $T_{1-37}$ by Cyanogen Bromide Cleavage

A sample of E. coli thioredoxin was dialyzed in water for 12 hr at 4° C. Five ml was dried and resuspended in 70% formic acid. Cyanogen bromide (Sigma Chemical) was dissolved in 70% formic acid and added to thioredoxin in a 50-fold molar excess of methionine. The solution was purged with nitrogen and incubated at room temperature in the dark for 24 hr. At the completion of the cleavage reaction the solution was dried under nitrogen, resuspended in sodium acetate buffer and adjusted to pH 8.5 with ammonium hydroxide.

Samples were loaded onto a Waters μ-Bondapak C-18 column (Trademark of Waters Associates, Inc., Milford, Mass.) attached to a Beckman Model 421 system (Trademark of Beckman Instruments, Inc., Fullerton, Calif.) monitored at 214 nm. The solvent system employed was 0.1% trifluoroacetic acid (Buffer A) and 0.08% trifluoroacetic acid in acetonitrile (Buffer B). A gradient from 0% to 60% B over 30 min was used to separate the peptides at a flow rate of 2 ml/min.

Thioredoxin was cleaved by CNBr into two fragments, $T_{1-37}$ and $T_{38-108}$, eluting at 44% and 51% buffer B, respectively. Amino acid analysis identified and confirmed the composition of both peptides. (Holmgren, A. and Reichard, P. [1967] Eur. J. Biochem. 2, 187–196). $T_{1-37}$ contained the active site of the enzyme. The two peptides recovered accounted for 69% of the starting material. Unreacted thioredoxin accounted for 12–15% of the loss, while HPLC separation may be responsible for the additional losses.

(b) Production of $T_{19-36}$ by Trypsin Cleavage

After HPLC separation, described above, $T_{1-37}$ was pooled, dried, and resuspended in sodium acetate buffer and adjusted to pH 8.0 with $NH_4OH$. An aliquot of trypsin (Sigma Chemical) was added to the incubation at 1% (w/w) of peptide concentration. The reaction mixture was incubated at 37° C. for 1 hr. Separation of trypsin fragments was done by HPLC as for the cyanogen bromide fragments.

Trypsin digestion of the $T_{1-37}$ peptide yielded two peptides, $T_{4-18}$ and $T_{19-36}$, which were resolved by HPLC, eluting at 31% and 45% in buffer B, respectively. Amino acid analysis revealed that the species eluting at 31% B contained 15 amino acids and corresponds to the active site peptide, $T_{19-36}$. Incubation of 90 nmoles of $T_{1-37}$ produced 80 nmoles $T_{19-36}$ after separation by HPLC with a yield of 88%.

Following are examples which illustrate products of the invention and procedures, including the best mode, for practicing the invention. These examples should not be construed as limiting. All percentages are by weight and all solvent mixture proportions are by volume unless otherwise noted.

EXAMPLE 1

Maintenance and Growth of Bacterial and Phage Strains

E. coli strain SK3981 containing plasmid pBHK8 was constructed as described previously (Lunn et al.) and is available from the permanent collection of the Northern Regional Research Laboratory, U.S. Department of Agriculture, Peoria, Ill. 61604, USA. The deposit was made on Nov. 8, 1985, and the repository accession number is NRRL B-18027. E. coli strain JM103 and the phage MP19 were obtained from New England Biolabs. These bacterial strains were grown in YT medium (5 g/l yeast extract, 10 g/l bactotryptone, 5 g/l NaCl). Medium was supplemented with 50 mg/l ampicillin for growth of SK3981.

EXAMPLE 2

Propagation and Isolation of Phage DNA

Preparation of M13 derived recombinant phage stocks and isolation of phage DNA was done using previously described procedures (Messing, J. [1983] Methods Enzymol. 101:20–78).

EXAMPLE 3

Preparation of Synthetic Oligonucleotides

Synthetic oligonucleotides were prepared using automated synthesis with an Applied Biosystems (Foster City Calif.) 380A DNA synthesis machine.

EXAMPLE 4

DNA Tranformation of E. coli Cells

E. coli JM103 competent for DNA transformation were prepared as described by a commonly used procedure (Cohen, S. N., Chang, A. C. P. and Hsu, L. [1972] Proc. Natl. Acad. Sci. USA 69:2110–2114). Heteroduplex recombinant phage DNA (60 ng) was added to 0.2 ml of competent JM103 and held at 0° C. for 15 min. The cells were pulsed at 42° C. for 2 min and 20 μl was added to 3 ml of YT broth containing 0.7% bacto agar and 0.2 ml of an overnight culture of JM103. The mixture was spread on a YT agar plate (YT broth plus 1.5% bacto agar) and the plates were incubated overnight at 37° C.

EXAMPLE 5

Restriction Enzyme Digestion

All restriction enzymes were purchased from either Bethesda Research Labs (Gaithersburg, Md.) or New England Biolabs. Incubation conditions were those recommended by the manufacturer.

EXAMPLE 6

Ligation of DNA Fragments

DNA ligation reactions (20 μl) contained 60 mM Tris-HCl, pH 7.5, 10 mM $MgCl_2$, 1 mM dithiothreitol, 50 μM ATP, 20 nM DNA termini and 20 units T4 DNA ligase (New England Biolabs). Incubation was at 14° C. for 4 hr.

EXAMPLE 7

DNA Sequencing

DNA sequencing of thioredoxin and thioredoxin derivatives was done by the chain termination method of Heidecker et al. (Heidecker, G. Messing, J. and Gronenborn, B. [1980] Gene 10:68–73). The oligonucleotide 5' ATTCACCTGACTGAC was used to prime the sequencing reactions.

EXAMPLE 8

Isolation of Recombinant MP19 Containing the Thioredoxin Gene

Ligation of plasmid pBHK8 digested with KpnI and PvuII, and MP19 digested with KpnI and HincII was done as described in Example 6. The DNA was transformed to competent JM103 as described in Example 4, except the YT plates contined IPTG (isopropyl thiogalactoside, Sigma) and Xgal (5-bromo-4-chloro-3-indolyl-$\beta$-D-galactoside, Sigma). Recombinant phage containing DNA inserts made clear plaques whereas MP19 phage makes blue plaques. Clear plaques were added to 2 ml of JM103 in YT broth and single strand DNA was prepared as described (Messing, J. [1983] Methods Enzymol. 101: 20–78). Those clones containing large DNA inserts were identified using agarose gel electrophoresis by virtue of their slower mobility. That these clones contained the thioredoxin gene was confirmed by sequencing the single strand DNA by the dideoxy chain termination method.

EXAMPLE 9

Formation of Heteroduplex DNA Containing A Mismatched Basepair

A 27-base oligonucleotide 5'-TGG TGC GGT CCG AGC AAA ATG ATC GCC was kinased with T4 polynucleotide kinase and ATP as described by Maniatis et al. (Maniatis, T., Fritsch, E. F. and Sambrook, J. [1982] Molecular Cloning: A Laboratory Manuall Cold Spring Harbor Laboratory, Cold Spring Harbor, N.Y.). Recombinant phage DNA containing the antisense strand of thioredoxin gene was used as substrate to form heteroduplex DNA.

A mixture (60 $\mu$l) containing 20 mM Tris-HCl, pH 7.5, 7 mM $MgCl_2$, 1 mM dithiothreitol, 50 mM NaCl, 0.4 $\mu$g phage DNA, 10 ng oligonucleotide was heated at 68° C. for 15 min, then 37° C., 10 min and placed at 0° C. The following additions were made: dATP, dCTP, dTTP, GTP to 0.2M; ATP to 1M; 4 units of DNA Polymerase I Klenow (New England Biolabs); 0.5 $\mu$g of E. coli single strand binding protein (Pharmacia, Piscataway, N.J.); 20 units T4 DNA ligase (New England Biolabs). The mixture was incubated at 14° C. for 4 hr. The DNA was transformed to JM103 competent cells and plated as described in Example 4.

EXAMPLE 10

Differential Hybridization of DNA on Nitrocellulose Filters

Phage DNA was prepared from individual clones obtained from cell transformation with heteroduplex DNA. About 0.3 $\mu$g of each was placed on a nitrocellulose sheet (Schleicher and Schuell, Keene, N.H.) and the sheet baked for 2 hr at 68° C. The filter was prehybridized in 5 ml 6X SSC (1X SSC=0.15M NaCl, 0.015M sodium citrate, 1 mM EDTA) and 10X Denhardt's solution (100 X—2% bovine serum albumin, 2% ficoll, 2% polyvinyl pyrolidone) for 15 min at 23° C. The filter was placed in a sealable bag with 5 ml of hybridization solution containing $5 \times 10^6$ $^{32}$P-cpm ($10^8$cpm/$\mu$g) oligonucleotide (5'-$^{32}$P-C GGT CCG AGC AAA AT) in 6X SSC+10X Denhardt's solution. Hybridization was at 23° C. for 1 hr. The filter was washed three times at 23° C. for 15 min with 6X SSC. The filter was washed once with 50 ml 6X SSC at 42° C. for 5 min and autoradiographed for 2 hr. The filter was then washed with 50 ml 6X SSC at 60° C. for 5 min and autoradiographed overnight. Clones that showed hybridization at 60° C. as well as at 42° C. were further analyzed by sequencing.

EXAMPLE 11

Formation and Restriction of Duplex DNA from Single Stranded Phage DNA

Gene constructions in recombinant M13 phage can be transferred to plasmids for propagation and protein production. The same technique as described in Example 9 can be used to form duplex DNA. Restriction cleavage at sites flanking the gene can be used to obtain a duplex fragment for ligation into a suitable plasmid. For example, we have transferred the thioredoxin shufflease gene into the plasmid pUC18 (New England Biolabs).

Example 12

General Protocol for Obtaining Thioredoxin Shufflease Gene from a Thioredoxin Gene Source Oligonucleotide-directed mutagenesis can be used to create a thioredoxin shufflease gene from a thioredoxin gene source. We have shown an example in which Cys35 is replaced with serine. Other changes at codon 35 resulting in any amino acid replacement at this position can be accomplished with these techniques. These techniques can also be used to alter other codons in the gene which can result in shufflease molecules that are active at different pH or ionic conditions. The basic criterion of a thioredoxin shufflease is that the compound contains a single reactive thiol and it catalyzes the exchange of disulfides in a protein undergoing the refolding process.

EXAMPLE 13

Effect of Thioredoxin Shufflease on Refolding of Reduced and Denatured RNase

At pH 9.0 (0.1M Tris, 1.0 mM EDTA) thioredoxin shufflease or a mixture of thioredoxin shufflease and oxidized DTT increased the rate of refolding of RNase as compared to air oxidation alone. The presence of thioredoxin shufflease increases the rate of refolding by a factor of two. The time for 50% reactivation with air is 9 hr and only 4–5 hr with thioredoxin shufflease. The addition of oxidized DTT (5 mM) had no effect on the rate of refolding with thioredoxin shufflease at this pH. Under these conditions thioredoxin shufflease is 30-fold more effective in refolding reduced and denatured ribonuclease than is thioredoxin.

At pH 7.4 (0.1M Tris, 1 mM EDTA) thioredoxin shufflease significantly increased the rate of refolding as compared to air oxidation. The time for 50% reactivation with 5 $\mu$M thioredoxin shufflease was 51 hr, whereas the time for 50% reactivation in the presence of air could not be determined because of the slow rate of renaturation of RNase with no oxidant added.

The efficiency of RNase reactivation with 5 $\mu$M thioredoxin shufflease was comparable to the efficiency observed using 20 mM oxidized DTT. The time for 50% reactivation for 20 mM oxidized DTT in the presence of air was 56 hr. Similarly, in the presence of oxygen, the $T_{\frac{1}{2}}$ for 5 μM thioredoxin shufflease was 21 hr and 26 hr for 20 mM oxidized DTT.

In order to obtain maximal activity, thioredoxin shufflease requires the presence of an oxidant. When oxygen is used as the oxidant, the time for 50% reactivation is decreased from 51 hr to 21 hr as compared to air. Chemical oxidants such as oxidized DTT can also be used. In the presence of air, thioredoxin shufflease (5 μM) with oxidized DTT (20 mM) gave 50% reactivation of RNase after 20 hr. Similarly, in the presence of oxygen, the $T_{\frac{1}{2}}$ for thioredoxin shufflease with DTT was 11 hr, compared to 20 to 25 hr for either DTT or oxygen used individually.

The refolding of RNase catalyzed by 5 μM thioredoxin. shufflease in the presence of 20 mM DTT was comparable to that observed with 100 μM thioredoxin In the presence of air, 50% reactivation of RNase was obtained after 18 hr with thioredoxin shufflease and DTT. In the presence of oxygen, the $T_{\frac{1}{2}}$ was 11 hr for thioredoxin shufflease with DTT.

At pH 7.4, thioredoxin shufflease was 5,000-fold more effective than oxidized DTT. Thioredoxin shufflease in the presence of oxidized DTT was at least 20-fold more effective than thioredoxin.

EXAMPLE 14

Upon substituting thioredoxin shufflease, alone, or in combination with oxygen, for the DTT or DTE in the examples of U.S. Pat. No. 4,421,685, there is obtained an improved yield of the desired insulin.

EXAMPLE 15

Upon substituting any disulfide protein or S-sulfonated disulfide protein for the bovine pancreatic ribonuclease above exemplified, there are obtained comparable beneficial protein folding results.

EXAMPLE 16

Upon reacting an unfolded protein whose disulfide crosslinks have been reduced, with a mixture comprising an effective protein folding amount of thioredoxin shufflease and a thiol reducing agent, for example, dithiothreitol and dithioerythritol, there is obtained an enhanced folding of said protein.

EXAMPLE 17

Upon reacting an unfolded S-sulfonated disulfide protein with a mixture comprising an effective protein folding amount of thioredoxin shufflease and a thiol reducing agent, for example, dithiothreitol and dithioerythritol, there is obtained an enhanced folding of said protein.

EXAMPLE 18

At pH 8.5 (0.1M Tris, 1.0 mM EDTA) thioredoxin shufflease increased the rate of reactivation of scrambled RNase as compared to air oxidation alone. After 10 hr there was 25% reactivation of RNase in the presence of 5 μM thioredoxin shufflease and 50% with 10 μM thioredoxin shufflease. With no thioredoxin shufflease present, 10% RNase activity is recovered after 5 hr and no further increase is observed at 10 hr.

EXAMPLE 19

Refolding of Sulfonated RNase with Thioredoxin Shufflease

Thioredoxin shufflease efficiently catalyzed the refolding of sulfonated RNase at pH 7.5 to yield a quantative recovery of active RNase. Sulfonated RNase was prepared by the method of Thannhauser and Scheraga (Thannhouser, T. W. and Scheraga, H. A. [1985] Biochemistry 24:7681–7688). Reduced thioredoxin shufflease was required and the optimal conditions were a 1:1 molar ratio of thioredoxin to the protein thiosulfonates (8:1 molar ratio thioredoxin to RNase). When the ratio was decreased to 1:2 thioredoxin to protein thiosulfonates, both the rate of reactivation and the final yield of RNase activity decreased. At a 1:1 ratio, the $T_{\frac{1}{2}}$ (time required for 50% recovery of activity) was 3.5 hr and the final yield of RNase was 80%. When thioredoxin was decreased two-fold, the $T_{\frac{1}{2}}$ increased to 22 hr and the recovery of RNase activity was only 60%.

We claim:

1. An enzyme, thioredoxin shufflease, which is characterized by:
   (a) it is thioredoxin, or fragment of thioredoxin, wherein the Cys35 residue has been replaced with a serine residue;
   (b) it catalyzes the exchange of disulfides in a protein undergoing the refolding process; and
   (c) it is not consumed in the oxidation/refolding process.

2. A thioredoxin shufflease, according to claim 1, which is produced from an *E. coli* thioredoxin gene.

3. A thioredoxin shufflease, according to claim 2, wherein the *E. coli* thioredoxin gene is derived from *E. coli* strain SK3981.

4. A process for preparing thioredoxin shufflease wherein said thioredoxin shufflease has the characteristics described in claim 1; said process comprising changing, in a thioredoxin gene, the codon coding for Cys35 to a codon coding for serine, culturing a host organism comprising a recombinant DNA transfer vector comprising the changed thioredoxin gene, and isolating thioredoxin shufflease from the culture.

5. An in vitro process for folding an unfolded protein containing disulfide crosslinks which have been reduced which comprises reacting said unfolded and reduced protein with an effective protein folding amount of thioredoxin shufflease, wherein said thioredoxin shufflease has the characteristics described in claim 1, said thioredoxin shufflease may be used alone or in combination with oxygen.

6. A process, according to claim 5, whererin said effective protein folding amount of oxidized thioredoxin shufflease is about 3 μM to about 50 μM.

7. A process, according to claim 5, wherein the process is conducted at a pH of about 7.0 to about 11.0.

8. A process, according to claim 5, wherein said protein containing disulfide crosslinks is selected from the group consisting of insulin, proinsulin, bovine pancreatic ribonuclease (RNase), lysozyme, bovine pancreatic trypsin inhibitor, interferon, rennin, plasminogen activator, prolactin, human α-1 tryspin inhibitor, and Factor VIII.

9. An in vitro process for folding an unfolded protein whose disulfide crosslinks have been reduced which comprises reacting said unfolded and reduced protein with a mixture comprising an effective protein folding amount of thioredoxin shufflease, and a thiol oxidizing agent wherein said thioredoxin shufflease has the characteristics described in claim 1.

10. A process, according to claim 9, wherein said thiol oxidizing agent is oxidized dithiothreitol or dithioerythritol.

* * * * *

UNITED STATES PATENT AND TRADEMARK OFFICE
CERTIFICATE OF CORRECTION

PATENT NO. : 4,904,602

DATED : February 27,1990

INVENTOR(S) : Vincent P. Pigiet, James R. Rusche, Barbara J. Schuster

It is certified that error appears in the above-identified patent and that said Letters Patent is hereby corrected as shown below:

| | | |
|---|---|---|
| Column 9: | line 12: | "contined IPTG" should read --contained IPTG--. |
| | line 33: | "Laboratory Manuall" should read --Laboratory Manual;--. |
| | line 44: | "GTP" should read --dGTP--. |
| | line 44: | "0.2M" should read --0.2mM--. |
| | line 44: | "1M" should read --1mM--. |
| Column 11: | line 15: | "thioredoxin.shufflease" should read --thioredoxin shufflease--. |
| | line 16: | "thioredoxin In" should read --thioredoxin.In--. |
| Column 12: | line 46: | "whererin" should read --wherein--. |

Signed and Sealed this

Twenty-fourth Day of December, 1991

*Attest:*

HARRY F. MANBECK, JR.

*Attesting Officer*  *Commissioner of Patents and Trademarks*